United States Patent
Bowman et al.

(10) Patent No.: US 6,580,001 B1
(45) Date of Patent: Jun. 17, 2003

(54) METHOD OF MAKING TRIMETHYLENE CARBONATE

(75) Inventors: Mark P. Bowman, New Kensington, PA (US); Charles B. Kreutzberger, Harrison City, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 10/029,728

(22) Filed: Dec. 20, 2001

(51) Int. Cl.⁷ .............................................. C07C 69/96
(52) U.S. Cl. ...................................... 558/260
(58) Field of Search ........................... 549/228; 558/260

(56) References Cited

U.S. PATENT DOCUMENTS

| | | | | |
|---|---|---|---|---|
| 4,365,055 A | | 12/1982 | Madigan ..................... | 528/371 |
| 4,384,115 A | | 5/1983 | Renga .......................... | 544/97 |
| 5,023,346 A | * | 6/1991 | Schon et al. | |
| 5,091,543 A | | 2/1992 | Grey .......................... | 549/228 |
| 5,212,321 A | | 5/1993 | Muller et al. ............... | 549/228 |

FOREIGN PATENT DOCUMENTS

| | | |
|---|---|---|
| JP | 94126269 | 6/1994 |
| JP | 94126271 | 6/1994 |

OTHER PUBLICATIONS

T. Ariga et al., *Macromolecules*, "Cationic Ring–Opening Polymerization of Cyclic Carbonates with Alkyl Halides to Yield Polycarbonate without the Ether Unit by Suppression of Elimination of Carbon Dioxide", 30 (1997) pp 737–743.

W. H. Carothers et al., Studies on Polymerization and Ring Formation. III Glycol Esters of Carbonic Acid:, *J. Am. Chem. Soc.*, 52 (1930) pp 314–326.

D. Saunders et al., "The Reaction of Oxygen Atoms with Tetrafluoroethylene", *J. Am. Chem. Soc.*, 87 (1965) pp 2088–2092.

U.S. Ser. No. 10/029,729, filed Dec. 20, 2001, Method of Making Trimethylene Carbonate, Mark P. Bowman and Charles B. Kreutzberger.

* cited by examiner

*Primary Examiner*—Joseph K. McKane
*Assistant Examiner*—Sonya Wright
(74) *Attorney, Agent, or Firm*—Dennis G. Millman

(57) ABSTRACT

A method of synthesizing trimethylene carbonate, which includes the steps of reacting 1,3-propanediol and phosgene in vapor form, providing a combination of temperature and pressure at which trimethylene carbonate is in its vapor phase, providing a residence time sufficient to react 1,3-propanediol and phosgene to trimethylene carbonate, condensing the trimethylene carbonate vapors, and isolating the condensed trimethylene carbonate.

The present method advantageously does not require the use of catalysts and the associated expense of recovering and/or recycling or disposing of catalyst residues.

24 Claims, 1 Drawing Sheet

METHOD OF MAKING TRIMETHYLENE CARBONATE

BACKGROUND OF THE INVENTION

The present invention is directed to a method of producing cyclic carbonic acid esters. More particularly, the present invention is directed to achieving a low-cost method of producing trimethylene carbonate.

Cyclic carbonic acid esters are used, for example, as building blocks of potentially biodegradable polymers. A particular cyclic carbonic acid ester, trimethylene carbonate (trimethylene carbonate or 1,3-dioxan-2-one), may be used in a variety of applications, such as for surgical stitching material, vessel implants, and apparatus for osteo-synthesis. Trimethylene carbonate is a desirable monomer to use because of its property of not decreasing in volume on polymerization.

Trimethylene carbonate may be used as a monomer in the synthesis of poly(trimethylene carbonate) polyols, which are used in flexibilizing acrylic melamine coatings. Trimethylene carbonate may also be used to make surgical sutures and modified polyurethane elastomers. Poly(trimethylene carbonate) polyols improve both ambient and low temperature flexibility and reduced the viscosity of urethane coatings formulated with selected commercial acrylic polyols.

For industrial production of trimethylene carbonate, it would be desirable to find a method of synthesis yielding cyclic carbonates in high yields by a relatively simple industrial process. Numerous methods are known for producing carbonic acid esters, such as trimethylene carbonate. For example, the transesterfication of diethylcarbonate with 1,3-propanediol in the presence of sodium or sodium methoxide to obtain trimethylene carbonate is one of the oldest methods of production (W. H. Carothers et al., *J. Am. Chem. Soc.*, 52 (1930) 322), but the purity of the product obtained is not sufficient for use in polymerization reactions, which results in a lower grade product. In addition, the low yield makes this method unattractive for industrial use.

U.S. Pat. No. 5,212,321 to Muller et al. discloses a method for producing trimethylene carbonate where 1,3-propanediol is reacted with diethylcarbonate in the presence of zinc powder, zinc oxide, tin powder, tin halide, or an organo-tin compound, at an elevated temperature. However, the Muller et al. process is very expensive as the process, the separation, isolation, and disposal of residues and catalysts or catalyst material are time-consuming and expensive.

U.S. Pat. No. 5,091,543 to Grey discloses a method of preparing five- and six-membered cyclic carbonates. The method involves reacting a 1,2- or 1,3-diol with an acyclic diester of carbonic acid in the presence of a catalyst selected from alkylammonium salts, tertiary amines, and ion-exchange resins containing alkylammonium or tertiary amino groups. Cyclic carbonates free of polycarbonate by-products are obtained in high yields. However, the Grey process is also very expensive, as the process requires the use of reactors made from materials of construction that will not corrode when exposed to the halide ions in the process. Isolation and disposal of residues and catalysts are also time-consuming and expensive.

Another process used to prepare trimethylene carbonate involves reacting 1,3-propanediol with urea in the presence of zinc-based catalysts. This type of process is described, for example, in Japanese Patent Nos. 7-330686 and 7-330756. The process requires expensive and time-consuming isolation, recovery, and recycling of the catalysts.

Trimethylene carbonate has also been made by reacting 1,3-propanediol with ethylchloroformate while using two equivalents of triethylamine (Toshiro Agriga et al., *Macromolecules*, 30 (1997) 737). However this method produces trimethylene carbonate in low yield and requires large amounts of triethylamine.

The vapor-phase reaction between phosgene and an alcohol is known to form the corresponding chloroformate (Saunders et al., *J. Am. Chem. Soc.*, 87 (1965) 2088). Continuous processes for the formation of chloroformates from phosgene and alcohols are disclosed in Japanese Patent Nos. JP 51-043719 and JP 51-043721.

There remains a need for a low-cost method for producing trimethylene carbonate. A low-cost method desirably involves production of trimethylene carbonate in relatively high yields with reduced expenses for clean up and/or recycling or disposing of residues and/or catalyst material. A combination of several or all of these desirable features would be even more desirable.

SUMMARY OF THE INVENTION

The present invention is directed to a novel method of synthesizing trimethylene carbonate. The method comprises reacting 1,3-propanediol and phosgene in vapor form while providing a combination of temperature and pressure at which trimethylene carbonate boils or is in a vapor phase, and providing a residence time at those conditions sufficient to react at least some of the 1,3-propanediol and phosgene to trimethylene carbonate.

An advantage of the method of the present invention is that it does not require the use of catalysts and their associated expense of recovery and recycling or disposing of catalyst residues. Although not required, the use of catalysts is not precluded in the method of the present invention if desired.

DETAILED DESCRIPTION OF THE INVENTION

Figure 1:
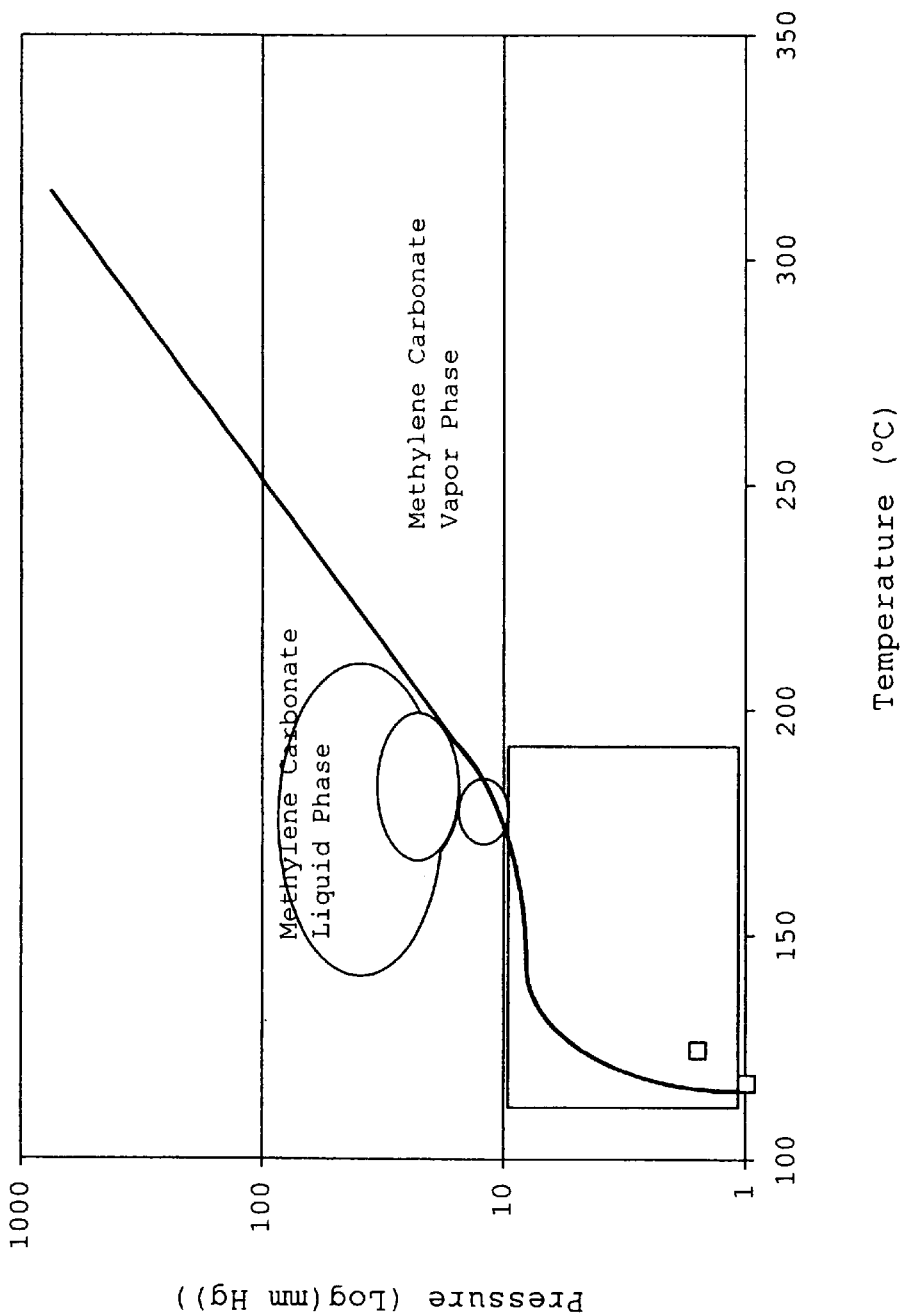
FIG. 1 is a plot of the relationship between the boiling temperature of trimethylene carbonate and pressure.

Unless otherwise indicated, all numbers or expressions referring to quantities of ingredients, reaction conditions, etc. used herein are to be understood as modified in all instances by the term "about." All references to pressure refer to absolute pressure unless otherwise indicated.

In the method of synthesizing trimethylene carbonate of the present invention, 1,3-propanediol and phosgene are reacted in vapor form in an appropriate reaction vessel. The proportion of the reactants is most efficiently at or near stoichiometric amounts, but theoretically any amounts can be used. It may be preferred in some cases to employ an excess of phosgene to minimize any unreacted 1,3-propanediol in the product stream, thereby reducing the likelihood of unwanted reactions downstream from the reaction zone. In particular embodiments of the invention, the molar ratio of 1,3-propanediol to phosgene provided to the reaction zone is from 1.0:0.7 to 1.0 to 20, typically from 1.0:0.7 to 1.0:10, and more typically from 1.0:0.7 to 1.0:2.0. When 1,3-propanediol and phosgene are outside of these ranges, the conversion to trimethylene carbonate may be so low as to not be practical for industrial requirements.

In addition to phosgene, phosgene equivalents can be used in the present method. Phosgene equivalents that can be used in the present invention include, but are not limited to, diphosgene and triphosgene. Phosgene equivalents decompose to form phosgene in situ, but are preferable in some cases due to their ease of handling on a commercial scale compared to phosgene.

Gas phase phosgenation of 1,3-propanediol is advantageous in that intermolecular reactions that generate trimethylene carbonate oligomers are minimized. An appropriate combination of temperature and pressure is provided in the present invention in order to maintain the 1,3-propanediol above its boiling point (214° C. at atmospheric conditions) and also to maintain the trimethylene carbonate that is formed in the vapor state in the reaction zone. An estimated boiling point of trimethylene carbonate is determined as described below.

As is known from the basic gas laws, temperature and pressure are inversely related to each other at the boiling point of trimethylene carbonate. FIG. 1 shows an approximate curve defining the relationship of the boiling temperature of trimethylene carbonate with pressure, based on five known data points. Vapor phase conditions for trimethylene carbonate include any combination of temperature and pressure on or to the right of the curve in FIG. 1. Temperatures above the boiling point for a given pressure can be used in the present invention; however, to reduce the likelihood of competing reactions, temperatures of approximately 400° C. are preferably avoided in some embodiments. At atmospheric pressure, trimethylene carbonate has a boiling point of approximately 315° C.

Although a wider range of temperatures and pressures are theoretically possible, the reaction of the present method is typically carried out at temperatures ranging from about 100° C. to about 400° C., with pressures within the reaction vessel between about 1 mm and about 800 mm Hg. In an embodiment of the present invention, the reaction is carried out at sub-atmospheric pressures. Typical sub-atmospheric pressures employed in embodiments of the invention include pressures less than 300 mm Hg, less than 200 mm Hg, less than 100 mm Hg, or less than 20 mm Hg. Lower pressures are preferred in most cases because the reaction then can be run at a lower temperatures, whereby fewer competing reactions are likely to take place.

The residence time in the reaction zone for reacting 1,3-propanediol and phosgene to form trimethylene carbonate and is typically a function of the starting reactant feed rates and the temperature. The residence time can vary considerably, and with some embodiments may range from about 1 to 600 seconds, typically 1 to 30 seconds in the particular embodiments described herein, and most typically 5 to 20 seconds.

The residence time can be shortened by employing a non-reactive sweeping gas to carry the reactants and reaction products through the reactor. Suitable non-reactive gasses include, but are not limited to, nitrogen and the inert gases neon, argon, krypton, xenon, and helium. Nitrogen is a preferred gas due to its low cost.

The trimethylene carbonate vapors in the reaction product stream may be condensed after leaving the reaction vessel. The condensation is accomplished by exposing the trimethylene carbonate vapor to a liquid phase condition (any location to the left of the curve in FIG. 1). Condensation of the trimethylene carbonate not only recovers the product but also serves to separate the trimethylene carbonate from HCl vapors in the product stream. Accomplishing this separation as soon as possible after reaction is desirable for minimizing unwanted reaction of trimethylene carbonate with HCl. Generally, a condenser is used, in which trimethylene carbonate is condensed from the vapor phase to the liquid phase and HCl exits the condenser as a vapor. The inert gas flow aids in separating and removing the HCl vapor from the trimethylene carbonate. The condensed trimethylene carbonate is isolated once condensed.

The trimethylene carbonate can be isolated in any type of container that is free of active hydrogen containing compounds. Active hydrogen containing compounds, such as water, HCl, or alcohols, can react with the condensed trimethylene carbonate.

Suitable containers include heated bulk storage tanks (temperature above the melting temperature of trimethylene carbonate, 47° C.). The condensed trimethylene carbonate can also be placed in a drum or a tote and allowed to solidify therein.

The present method may include the additional step of solidifying the condensed trimethylene carbonate for additional processing. In this situation, the solidified trimethylene carbonate is further processed so it can be easily handled as a solid material. An example of further processing includes, but is not limited to, milling the solidified trimethylene carbonate into granular or powder form.

The present invention is more particularly described in the following examples, which are intended to be illustrative only, since numerous modifications and variations therein will be apparent to those skilled in the art. Unless otherwise specified, all parts and percentages are by weight.

EXAMPLE 1

A vertical glass tube, 2 centimeters in diameter and 22 centimeters in length, was packed with ⅛-inch glass helices. The void volume within the packed glass tube was 49.7 ml and the glass helices occupied 21.4 ml. The glass tube was wrapped with electric heating tape. A thermocouple was placed one-third of the way down the glass tube between the glass and the heating tape. The feed of 1,3-propanediol was allowed to slowly drip from a dropping funnel onto the top of the hot packing within the tube.

Phosgene and nitrogen were also introduced at the top of the hot tube. The downflow, gaseous concurrent flow of phosgene, nitrogen, and 1,3-propanediol vapor passed through the hot tube and reaction products were condensed at ambient temperatures and analyzed by gas chromatography.

Four grams of 1,3-propanediol was added over 15 minutes to the hot tube maintained at 325° C. Simultaneously over this 15 minute period, 15 grams of phosgene gas was also fed into the hot tube. Additionally, nitrogen was swept through the hot tube at 25 ml/min. The condensate was analyzed by gas chromatography to contain 24.0% by weight trimethylene carbonate.

EXAMPLE 2

The method and apparatus of Example 1 was used to prepare trimethylene carbonate. Three grams of 1,3-propanediol was added over 11 minutes to the hot tube maintained at 325° C. Simultaneously, over this 11 minute span, 19 grams of phosgene gas was also fed into the hot tube. Additionally, nitrogen was swept through the hot tube at 56 ml/min. The condensate was analyzed by gas chromatography and found to contain 40.2% trimethylene carbonate.

EXAMPLE 3

The method and apparatus of Example 1 was used to prepare trimethylene carbonate. Six grams of 1,3- propanediol were added over 15 minutes to the hot tube maintained at 250° C. Simultaneously, over this 15 minute span, 22 grams of phosgene gas were also fed into the hot tube. Additionally, nitrogen was swept through the hot tube at 86 ml/min. The condensate was analyzed by gas chromatography and found to contain 40.8% by weight of trimethylene carbonate.

EXAMPLE 4

The method and apparatus of Example 1 was used to prepare trimethylene carbonate. Two grams of 1,3-propanediol were added over 7 minutes to the hot tube maintained at 300° C. Simultaneously, over this 7 minute span, 7.7 grams of phosgene gas were also fed into the hot tube. Additionally, nitrogen was swept through the hot tube at 86 ml/min. The condensate was analyzed by gas chromatography and found to contain 43.8% by weight of trimethylene carbonate.

Separation of trimethylene carbonate from the remainder of the reaction products in the condensate in the examples set forth above can be accomplished by conventional techniques known to those of skill in the art, including distillation or crystallization.

In the examples set forth above, the 1,3-propanediol was fed into the reaction zone as a liquid and vaporized by contact with the hot packing material. It should be apparent that an alternative approach would entail vaporizing the 1,3-propanediol in a separate location and conveying the vapors into the reaction zone.

The invention has been described with reference to the preferred embodiments. Obvious modifications and alterations will occur to others upon reading and understanding the detailed description. It is intended that the invention be construed as including all such modifications and alterations insofar as they come within the scope of appended claims or the equivalents thereof.

We claim:

1. A method of synthesizing trimethylene carbonate comprising:
   (a) contacting vaporous 1,3-propanediol with phosgene gas in a reaction zone;
   (b) providing in the reaction zone a combination of temperature and pressure at which trimethylene carbonate is in its vapor phase; and
   (c) providing within the reaction zone a residence time for the combined reactants of (a) at the conditions of (b) that is sufficient to allow 1,3-propanediol and in phosgene to form trimethylene carbonate.

2. The method of claim 1 wherein the phosgene is generated from a compound that decomposes to produce phosgene.

3. The method of claim 1, wherein the reactants and reaction products are carried by a non-reactive gas flow.

4. The method of claim 3, wherein the gas comprises nitrogen.

5. The method of claim 1, wherein the temperature in (b) is from 100° C. to 400° C. and the pressure is between 1 mm and 800 mm of mercury.

6. The method of claim 1, wherein trimethylene carbonate product vapors are condensed and the condensed trimethylene carbonate is permitted to solidify.

7. The method of claim 1, wherein the molar ratio of 1,3-propanediol to phosgene provided in (a) is from 1.0:0.7 to 1.0:20.

8. The method of claim 1, wherein the residence time in (c) is from 1 to 600 seconds.

9. The method of claim 2, wherein the compound from which the phosgene is generated is selected from the group consisting of diphosgene, triphosgene, and mixtures thereof.

10. The method of claim 6, wherein the solidified trimethylene carbonate is milled into granular or powder form.

11. A method of synthesizing trimethylene carbonate comprising the steps of:
    (a) reacting 1,3-propanediol and phosgene in a reaction zone in the vapor phase in the presence of a flowing non-reactive gas, wherein the molar ratio of 1,3-propanediol to phosgene is from 1.0:07 to 1.0:2.0, and wherein the temperature within the reaction zone is from 100° C. to 400° C., and the pressure in the reaction zone is less than 20 mm of mercury;
    (b) providing in the reaction zone a combination of said temperature and pressure at which combination trimethylene carbonate is in its vapor phase; providing within the reaction zone a residence time sufficient to allow 1,3-propanediol and phosgene to form trimethylene carbonate, said residence time being from 1 to 30 seconds; and
    (c) condensing vapors of trimethylene carbonate.

12. The method of claim 11, wherein the condensed trimethylene carbonate is permitted to solidify.

13. The method of claim 12, wherein the solidified trimethylene carbonate is milled into granular or powder form.

14. The method of claim 11, wherein the source of phosgene is selected from the group consisting of diphosgene and triphosgene.

15. The method of claim 11 wherein no catalyst is used to react 1,3-propanediol with phosgene.

16. A method of synthesizing trimethylene carbonate comprising:
    (a) contacting vaporous 1,3-propanediol with phosgene gas in a reaction zone;
    (b) providing in the reaction zone a combination of temperature and pressure at which trimethylene carbonate is in its vapor phase;
    (c) providing within the reaction zone a residence time for the combined reactants of (a) at the conditions of (b) that is sufficient to allow 1,3-propanediol and phosgene to form trimethylene carbonate;
    (d) removing reaction product containing trimethylene carbonate from the reaction zone; and
    (e) condensing trimethylene carbonate.

17. The method of claim 16 wherein the reactants and reaction product are carried by a non-reactive gas flow.

18. The method of claim 17 wherein the non-reactive gas comprises nitrogen.

19. The method of claim 16 wherein the temperature and pressure in (b) is from 100° C. to 400° C., and between 1 mm and 800 mm of mercury respectively.

20. The method of claim 16 wherein the molar ratio of 1,3-propanediol to phosgene charged to the reaction zone in (a) is from 1.0:0.7 to 1.0:20.

21. The method of claim 17 wherein the temperature and pressure in (b) is from 100° C. to 400° C., and between 1 mm and 800 mm of mercury respectively, and the molar ratio of 1,3-propanediol to phosgene charged to the reaction zone in (a) is from 1.0:0.7 to 1.0:20.

22. A method of synthesizing trimethylene carbonate comprising the steps of:

(a) reacting 1,3-propanediol and phosgene in a reaction zone in the vapor phase in the presence of a flowing non-reactive gas, wherein the molar ratio of 1,3-propanediol to phosgene is from 1.0:07 to 1.0:10, and wherein the temperature within the reaction zone is from 100° C. to 400° C., and the pressure in the reaction zone is from 1 mm to 800 mm of mercury;

(b) providing in the reaction zone a combination of said temperature and pressure at which trimethylene carbonate is in its vapor phase; providing within the reaction zone a residence time sufficient to allow 1,3-propanediol and phosgene to form trimethylene carbonate, said residence time being from 1 to 600 seconds; and (c) condensing vapors of trimethylene carbonate.

23. The method of claim 22 wherein the non-reactive gas comprises nitrogen.

24. The method of claim 22 wherein the reaction of 1,3-propanediol with phosgene is non-catalytic.

* * * * *